(12) United States Patent
Levorse, Jr. et al.

(10) Patent No.: US 7,838,487 B2
(45) Date of Patent: Nov. 23, 2010

(54) MACROCYCLIC MUSK

(75) Inventors: Anthony T. Levorse, Jr., Westfield, NJ (US); Brett D. Newirth, Atlantic Highlands, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 514 days.

(21) Appl. No.: 11/623,425

(22) Filed: Jan. 16, 2007

(65) Prior Publication Data

US 2008/0171796 A1 Jul. 17, 2008

(51) Int. Cl.
*A61K 8/18* (2006.01)
*A61K 8/00* (2006.01)
*C07C 49/00* (2006.01)

(52) U.S. Cl. .................. 512/8; 512/27; 512/1; 568/376
(58) Field of Classification Search ............ 512/1, 512/8, 27; 568/376
See application file for complete search history.

(56) References Cited

U.S. PATENT DOCUMENTS

| | | | | |
|---|---|---|---|---|
| 6,200,254 | B1 * | 3/2001 | Lupo et al. | 512/8 |
| 6,340,775 | B1 * | 1/2002 | Jacquot et al. | 568/376 |
| 6,815,413 | B2 * | 11/2004 | Eh et al. | 512/27 |
| 2002/0055453 | A1 * | 5/2002 | Eh et al. | 512/8 |
| 2003/0049213 | A1 * | 3/2003 | Matsuda et al. | 424/59 |

FOREIGN PATENT DOCUMENTS

| | | |
|---|---|---|
| JP | 55031085 | 3/1980 |
| WO | WO 2006/079608 | 8/2006 |

OTHER PUBLICATIONS

Hubert, A.J. "Macrocyclic compounds. XI. A novel synthesis of civeton homologs" J. Chem. Soc. (Jan. 1, 1965). Chem. Society. Letchworth, GB, No. Dec, pp. 6679-6681.
EPO Search Report.

* cited by examiner

*Primary Examiner*—Milton I Cano
*Assistant Examiner*—Aaron Greso
(74) *Attorney, Agent, or Firm*—Elizabeth M. Quirk; XuFan Tseng; Joseph F. Leightner

(57) ABSTRACT

The present invention is directed to novel compounds of the structure

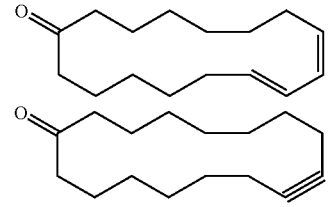

and a method for enhancing a perfume composition by incorporating an olfactory acceptable amount of the compounds provided above.

16 Claims, No Drawings

MACROCYCLIC MUSK

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by Structure II and V set forth below:

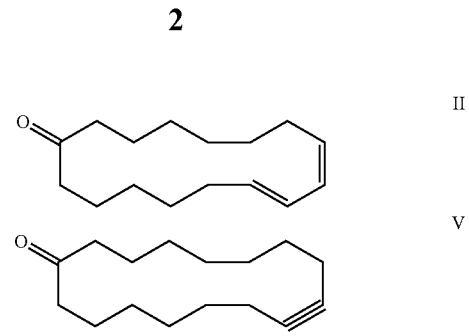

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

The compounds of the present invention may be prepared from the corresponding alkene isomers (E/Z) via an olefin halogenation then an elimination process by the following sequences:

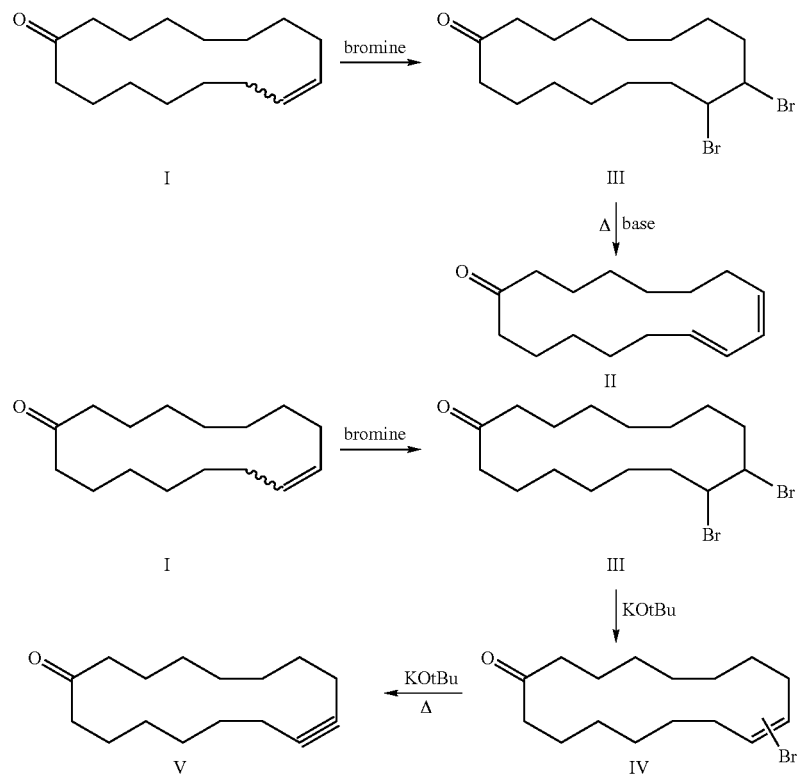

The starting material, 8-cyclohexadecenone, structure I, is available from Symrise GmbH & Co. and for the above, reagents are commercially available from Aldrich Chemical Company. 8,9-Dibromocyclohexadecanone, structure III and 8(9)-bromo-8-cyclohexadecenone, structure IV are intermediates which are not isolated but used as crude materials. KOtBu is understood by one skilled in the art to represent potassium tert-butoxide.

Those with skill in the art will recognize that some of the compounds of the present invention have a number of double bonds, thereby providing numerous geometric isomers of the claimed compounds (EE, EZ, ZE or ZZ). It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the fragrance compounds of Structure II and V impart naturalness to the fragrance formulations and are well suited for use as fragrance ingredients. 8-cyclohexadecynone (V) as a musk odorant and has warm, musky fragrance note. 7,9-cyclohexadecadien-1-one (II) has a warm, powdery, musky fragrance note.

According to one embodiment of the invention, an odorant or aroma mixture id provided comprising 7,9-cyclohexadecadien-1-one and 8-cyclohexadecenone. The weight ratio of 7,9-cyclohexadecadien-1-one and 8-cyclohexadecenone can be in the range preferably from 6:1 to 1:2, more preferably from 4:1 to 1:1.

The 1:1 mixture of 8-cyclohexadecenone and 7,9-cyclohexadecadien-1-one has a powerful, powdery musk fragrance note.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following examples are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE I

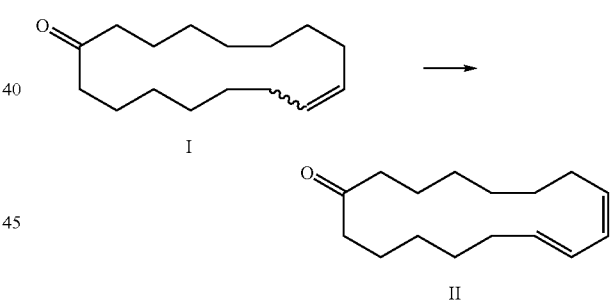

Preparation of 7,9-cyclohexadecadien-1-one (II)

A reaction flask was charged with 8-cyclohexadecenone, (236 g 1 mole), sodium acetate (10 g 0.1 mole) and dichloromethane (500 ml). The solution was cooled to 10° C. then bromine (240 g) was added over 2 hrs. The mass was warmed to room temp then washed with 500 ml of saturated aqueous sodium carbonate. The solvent was removed by rotary evaporation to give crude 8,9-dibromocyclohexadecanone (III).

The crude 8,9-dibromocyclohexadecanone was fed into a reaction vessel containing a slurry of dimethylformamide (DMF) 700 ml and lithium carbonate (111 g 1.5 mole) at 150° C. The mass was aged for 14 hrs. The reaction was washed with 2 L water then 10% aqueous acetic acid (500 ml). Distillation over caustic (2% NaOH) affords 54 g of 7,9-cyclohexadecadien-1-one and 86 g of a mixture of 8-cyclohexadecenone and 7,9-cyclohexadecadien-1-one.

Analytical Data for 7,9-cyclohexadecadien-1-one

Boiling point 166-168° C. at 3 mmHg
$H^1$NMR data: 1.19-1.44 ppm (m, 9H), 1.49-1.85 ppm (m, 5H), 1.98-2.24 ppm (m, 4H), 2.27-2.56 ppm (m, 4H), 5.17-6.37 ppm (m, 4H).

Odor character of 7,9-cyclohexadecadien-1-one: warm powdery musky note.

Odor character of 1:1 mixture of 8-cyclohexadecenone and 7,9-cyclohexadecadien-1-one: powerful, powdery musk note.

EXAMPLE II

Preparation of 8-cyclohexadecynone (V)

Crude 8,9-dibromocyclohexadecenone was prepared from 8-cyclohexadecenone in the example above, was fed into a reaction vessel containing xylene (1L), tert-butanol (1L) and potassium tert-butoxide (280 g 2.5 mole). The reaction was heated to reflux and aged for 6 hrs. The reaction was quenched with 10% aqueous acetic acid solution (500 ml ). The crude was flash distilled to give a mixture containing 8-cyclohexadecynone, 8-bromocyclohexadec-8-enone and 8-cyclohexadecenone. Fractional distillation afforded 35 g of 8-cyclohexadecynone.

Analytical Data for 8-cyclohexadecynone

Boiling point 153° C. at 2 mmHg
$H^1$NMR data: 1.28-1.39 ppm (m, 10H), 1.41-1.52 ppm (m, 8H), 1.60-1.73 ppm (m, 4H), 2.17-2.23 ppm (m, 4H), 2.40 ppm (t, 2H, J=2 Hz), 2.46 ppm (t, 2H, J=2 Hz).

Odor character of 8-cyclohexadecynone: warm musky note.

EXAMPLE 3

Fragrance formula: sweet/floral baby powder accord.

| | |
|---|---|
| Santaliff ® | 2.4 parts |
| Phenoxanol ® | 3.2 parts |
| Coumarin | 2.8 parts |
| Cyclamal Extra | 0.1 parts |
| Eth Vanillin | 0.7 parts |
| Geraniol 980 Pure | 0.1 parts |
| Hedione ® | 6.0 parts |
| Amy Cinnamic Aldehyde | 6.0 parts |
| Heliotropine | 1.7 parts |
| Hexyl Cinnamic Ald | 1.6 parts |
| Beta Ionone Extra | 0.6 parts |
| Iso E Super ® | 7.0 parts |
| Lyral ® | 1.6 parts |
| lillial ® | 16.0 parts |
| Lilianth | 2.0 parts |
| Methyl Ionone Gamma A | 7.3 parts |
| Veramoss | 0.2 parts |
| Peru Balsam Oil India | 0.3 parts |
| Prenyl Acetate | 0.1 parts |
| Methyl Cedryl Ketone | 4.0 parts |
| Methyl Phenyl Acetate | 0.1 parts |
| Aubepine | 0.4 parts |
| Benzoin | 1.0 parts |
| Cedrol Tex | 0.3 parts |
| Citronellol Extra | 0.3 parts |
| Geraniol Coeur | 0.4 parts |
| Methyl Cinnamate | 0.3 parts |
| Styrax Alva Ess | 0.2 parts |
| Vanillin ex Lignin | 1.2 parts |
| Cananga Java Native | 0.5 parts |
| Article claimed | 6.6 parts |

The above fragrance was prepared with a mixture of 7,9-cyclohexadecadien-1-one and 8-cyclohexadecenone (1:1 weight equivalent). An odor comparison was performed against the formula containing Globanone™ in place of the above mixture. Evaluation of the two fragrances indicated that the 7,9-cyclohexadecadien-1-one and 8-cyclohexadecenone fragrance was perceived to be stronger than the fragrance with Globanone™.

What is claimed is:

1. A method of improving, enhancing or modifying a fragrance formulation through the addition of an olfactory acceptable amount of 7,9-cyclohexadecadien-1-one.

2. The method of claim 1, wherein the fragrance formulation is incorporated into a product selected from the group consisting of a perfume, a cologne, a toilet water, a cosmetic product, a personal care product, a fabric care product, a cleaning product, and an air freshener.

3. The method of claim 1, wherein the olfactory acceptable amount is from about 0.005 to about 10 weight percent.

4. The method of claim 1, wherein the olfactory acceptable amount is from about 0.5 to about 8 weight percent.

5. The method of claim 1, wherein the olfactory acceptable amount is from about 1 to about 7 weight percent.

6. A fragrance formulation containing an olfactory effective amount 7,9-cyclohexadecadien-1-one.

7. A fragrance product containing 7,9-cyclohexadecadien-1-one.

8. An odorant or aroma mixture comprising 7,9-cyclohexadecadien-1-one and 8-cyclohexadecenone.

9. The odorant or aroma mixture of claim 8, wherein 7,9-cyclohexadecadien-1-one and 8-cyclohexadecenone have a weight ratio of from 6:1 to 1:2.

10. The odorant or aroma mixture of claim 8, wherein 7,9-cyclohexadecadien-1-one and 8-cyclohexadecenone have a weight ratio of from 4:1 to 1:1.

11. A method of improving, enhancing or modifying a fragrance formulation through the addition of an olfactory acceptable amount of the odorant or aroma mixture of claim 8.

12. The method of claim 11, wherein the fragrance formulation is incorporated into a product selected from the group consisting of a perfume, a cologne, a toilet water, a cosmetic product, a personal care product, a fabric care product, a cleaning product, and an air freshener.

13. The method of claim 11, wherein the olfactory acceptable amount is from about 0.005 to about 10 weight percent.

14. The method of claim 11, wherein the olfactory acceptable amount is from about 0.5 to about 8 weight percent.

15. The method of claim 11, wherein the olfactory acceptable amount is from about 1 to about 7 weight percent.

16. The method of claim 11, wherein 7,9-cyclohexadecadien-1-one and 8-cyclohexadecenone are provided in a 1:1 weight ratio.

* * * * *